United States Patent [19]

Grollier et al.

[11] Patent Number: 4,645,663.

[45] Date of Patent: Feb. 24, 1987

[54] PROCESS FOR PREPARING A HAIR DYE OR HAIR BLEACH COMPOSITION; A COMPOSITION FOR USE IN THIS PROCESS; AND THE USE OF SAID COMPOSITION TO DYE OR BLEACH HAIR

[75] Inventors: Jean-Francois Grollier, Paris; Christian Monnais, Neuilly-sur-Seine; Lyonel Peritz, Boulogne-sur-Seine, all of France

[73] Assignee: Societe Anonyme dite: L'Oreal, Paris, France

[21] Appl. No.: 768,721

[22] Filed: Aug. 23, 1985

Related U.S. Application Data

[62] Division of Ser. No. 365,023, Apr. 2, 1982, Pat. No. 4,555,246.

[30] Foreign Application Priority Data

Apr. 2, 1981 [FR] France ................................ 81 06676

[51] Int. Cl.4 ............................................... A61K 7/135
[52] U.S. Cl. ........................................ 424/62; 424/78; 424/81
[58] Field of Search ........................................... 424/62

[56] References Cited

U.S. PATENT DOCUMENTS 4,010,872 3/1977 Lozano et al. ......................... 424/62
4,465,663 8/1984 Schmolka .............................. 424/62
4,555,246 11/1986 Grollier et al. .......................... 8/405

Primary Examiner—Dale R. Ore
Attorney, Agent, or Firm—Cushman, Darby & Cushman

[57] ABSTRACT

A process for preparing a hair dye or bleach composition which comprises mixing a gelifiable liquid vehicle with an oxidizing solution having dissolved therein an incompatible cationic polymer. The resulting gel is applied to the hair and after an appropriate contact time, the hair is rinsed.

7 Claims, No Drawings

PROCESS FOR PREPARING A HAIR DYE OR HAIR BLEACH COMPOSITION; A COMPOSITION FOR USE IN THIS PROCESS; AND THE USE OF SAID COMPOSITION TO DYE OR BLEACH HAIR

This is a division of application Ser. No. 365,023, filed Apr. 2, 1982, now U.S. Pat. No. 4,555,246.

The present invention relates to a process for preparing a hair dye or bleach composition, to a composition resulting from this process and to the use of said composition resulting from this said process in the dyeing or bleaching of hair.

The principal activity of hair dye and hair bleaching compositions is known and is described in cosmetology literature, such as "Problèmes Capillaires", E. Sidi and C. Zviak, (Gauthier-Villard), Paris, 1966.

It is known that vehicles for hair dyes and hair bleaches are provided most often in the form of a cream, or in the form of a liquid, gelifiable on dilution.

Generally the creams are obtained either starting with soaps of $C_{12}$–$C_{18}$ fatty acids, or with a fatty alcohol in the presence of an anionic or non-ionic emulsifier and the gelifiable liquids are obtained either starting with polyoxyethylenated or polyglycerolated non-ionic compounds and solvents, or starting with soaps of liquid fatty acids and a solvent.

By admixing, with an oxidizing solution containing generally $H_2O_2$, in dilution ratios most often used (from 1 to 3 times), so that quantities of $H_2O_2$ and an alkaline agent (principally ammonia) are sufficient to obtain a lightening of the hair, the vehicles in the form of a cream produce a cream, and the vehicles in the form of a gelifiable liquid produce a gel.

The use of polycationic polymers (called hereafter, cationic polymers) in cosmetic compositions for the hair have already been envisaged, for example, in French patents or applications Nos. 1,429,597; 71.03017; 71.06387; 73.23970; 74.15162; 76.34076; 76.34077; 77.15088; 78.17899; 78.12942; 78.2704, as well as others.

The presence of these cationic polymers provide improved untangling of the hair, especially when the application of the cationic polymer is followed by shampooing the hair with an anionic detergent. Moreover, the hair thus treated is lively, shiny and the hair style has body or volume.

To effect dyeing or bleaching operations of the hair, specialists in this field prefer generally to apply the compositions in the form of a gel, since they are more easily applied and they impart to the hair more luminous glints or highlights and more beautiful shades.

It has been observed, however, that the compatibility of certain cationic polymers with the hair dyeing and bleaching vehicles or supports in the form of a gelifiable liquid, obtained starting with polyoxyethylenated or polyglycerolated non-ionic compounds and a solvent, was not totally acceptable. In some instances the vehicles were not clear and even were observed to contain some precipitated material at the expiration of a given period of time. These phenomena were of a nature to compromise the marketing of such a vehicle, especially if the storage thereof is a relatively long period of time. These cationic polymers, which are essentially useless as gelifiable supports, are called hereafter, by convention, "incompatible" cationic polymers.

There has now been discovered a process for preparing hair dye or hair bleach compositions which avoid these disadvantages and for using the said "incompatible" cationic polymers in compositions in the form of gels obtained starting with such gelifiable supports.

This process for the preparation of a hair dye or bleaching composition comprises mixing a gelifiable liquid vehicle with at least one cationic polymer and an oxidizing agent. An incompatible cationic polymer is employed and the said gelifiable vehicle is admixed with an oxidizing solution in which the incompatible cationic polymer is dissolved.

The gelifiable liquid vehicle is produced from one or several polyoxyethylenated or polyglycerolated non-ionic compounds and at least one solvent.

Representative non-ionic compounds include, in particular, natural or synthetic polyoxyethylenated or polyglycerolated fatty alcohols, principally those having 8 to 18 carbon atoms and most often 2 to 30 moles of ethylene oxide or 1 to 6 moles of glycerol, and polyoxyethylenated or polyglycerolated alkylphenols having, preferably 8 to 9 carbon atoms, and 2 to 30 moles of ethylene oxide or 4 to 6 moles of glycerol.

Representative polyoxyethylenated alkylphenols include the polyethers of nonylphenol polyoxyethylenated with 4–9 moles of ethylene oxide.

Representative polyglycerolated fatty alcohols include, in particular, oleyl alcohol polyglycerolated, for example, with 2 to 4 moles of glycerol.

Representative polyoxyethylenated fatty alcohols, include $C_9$–$C_{15}$ alcohols polyoxyethylenated for example with 3 to 10 moles of ethylene oxide.

Generally the hair dye or hair bleach vehicle contains from 5 to 60 percent by weight of the non-ionic compound.

The solvent used in the hair dye or hair bleaching composition is generally a water-miscible organic solvent.

Representative solvents include lower aliphatic alcohols, such as ethyl alcohol, propyl or isopropyl alcohol, glycols and glycol ethers, such as propylene glycol, the mono-methyl, mono-ethyl and mono-butyl ethers of ethylene glycol, dieythlene glycol, dipropylene glycol, hexylene glycol, diethylene glycol monoethyl ether, etc. and their mixtures.

Generally, these solvents of their mixtures are present in the hair dye or hair bleach vehicle in an amount of 2 to 20, and preferably 5 to 15, percent by weight.

The liquid gelifiable vehicle can also contain various conventional adjuvants.

These adjuvants can be fatty amides, natural or synthetic fatty alcohols, preservatives, sequestering agents and perfumes.

Representative fatty amides include, in particular, oleic or lauric diethanolamide and copra mono- or di-ethanolamide.

These amides are generally present in said vehicle in concentrations of 0.5 to 15 weight percent and, preferably, 10 weight percent.

Representative natural or synthetic fatty alcohols include, in particular, oleic, lauric, octyldodecyl, hexyldodecyl, isostearyl, ricinoleic and linoleic alcohols.

These alcohols are generally employed in the vehicle in amounts ranging from 1 to 25 percent and preferably, from 5 to 15 percent by weight.

The hair dye or hair bleach vehicles, based on non-ionic compounds, contain an alkalizing agent in an amount effective to obtain a pH of about 8 to 11 and preferably, 9.5 to 10.5.

The alkalizing agent present in the vehicles of this invention can be selected, for example, from the group consisting of soda, potash, ammonia, monoethanolamine, diethanolamine, triethanolamine, mono- or di-isopropanolamine, 2-amino-2-methyl-1,3-propanediol, 2-amino-2-methyl-1-propanol, and mixtures thereof.

When the vehicle is to be employed in the production of a hair dye composition, it also contains an oxidation dye.

It is known that oxidation hair dye compositions employ dyes called oxidation dyes which are aromatic compounds of the diamine, amino phenol or phenol type. These aromatic compounds are the dye precursors which are transformed into dye agents by condensation in the presence of a significant excess of an oxidizing agent, generally, $H_2O_2$.

Distinguished among the oxidation dyes, are, on the one hand, "bases" which are diamines or amino phenols (ortho or para derivatives) and on the other hand, "modifiers" often called "couplers" which are meta diamines, meta aminophenols or meta diphenols.

The "bases" principally employed are notably p-phenylenediamine, p-toluylenediamine, chloro-para-phenylenediamine, p-aminodiphenylamine, o-phenylenediamine, o-toluylenediamine, 2,5-diaminoanisole, o-aminophenol and p-aminophenol.

The "couplers" principally used are, notably, m-phenylenediamine, m-toluylenediamine, 2,4-diaminoanisole, m-aminophenol, pyrocatechol, resorcinol, α-naphthol, 1,5-dihydroxy naphthalene, 2,6-diaminopyridine and 2,4-diaminophenoxyethanol.

These oxidation dyes are generally present in the hair dye vehicle in an amount ranging from 0.002 to 15 percent by weight and preferably from 0.04 to 8 percent by weight. In addition to the oxidation dyes, the liquid gelifiable vehicle, when it is to be employed in the preparation of a hair dye composition, can also contain direct dyes such as the azo dyes, anthraquinone dyes, nitrobenzene dyes, indamines, indoanilines, and indophenols and the like.

Most often, the oxidizing solution contains $H_2O_2$ at a concentration of 20 to 60 volumes and preferably 20 to 30 volumes, and this oxidizing solution, containing $H_2O_2$ and the cationic polymer is added to the gelifiable liquid in a ratio of oxidizing solution to vehicle, ranging from 0.5 to 5 and, preferably, from 1 to 3 (by volume). The amount of the cationic polymer is such that the concentration of the cationic polymer in the final composition is between 0.01 and 10 weight percent and preferably between 0.05 and 5 weight percent.

It will be recalled that a solution of $H_2O_2$ at "n" volumes is a solution, one liter of which is capable of furnishing, under normal temperature and pressure conditions, n liters of oxygen by total decomposition according to the reaction: $H_2O_2 \rightarrow H_2O + \frac{1}{2}O_2$.

The cationic polymers employed in the process of the present invention are polymers containing units which include, either in the chains or in a lateral substituent, a tertiary or quaternary nitrogen atom, the said polymers being incompatible with the gelifiable vehicles obtained from non-ionic compounds and solvents.

To select the said incompatible polymers, it is sufficient, for example, to proceed with the following test:

There is introduced, at the desired concentration (in practice from 0.5 to 5 weight percent), for example 1% AM (active material) of a cationic polymer in the following support:

Nonylphenol oxyethylenated with 9 moles of ethylene oxide: 20 g
Nonylphenol oxyethylenated with 4 moles of ethylene oxide: 24 g
Monobutyl ether of ethylene glycol: 9 g
Propylene glycol: 10 g
Pentasodium salt of diethylene triamine pentacetic acid, (40% active material): 2.4 g
Ammonia, 22° Be': 10 g
Water, sufficient amount for: 100 g The appearance of a more or less accentuated cloud just up to precipitation (the precipitate in suspension immediately depositing on the walls of the container or in the course of storage after a few months) and/or the separation of the vehicle into two phases is the proof of the incompatibility of the cationic polymer in the non-ionic/solvent vehicle. An accelerated storage test can be used by storing the containers for 15 days at 45° C.

However, any other definition of the incompatible cationic polymers can be selected, the present invention applying, in a general manner, to any cationic polymer which, at the desired use concentration, gives a cloud or a precipitate when it is introduced in the selected gelifiable vehicle (based on non-ionic compounds and solvents).

Although the invention is not limited to the use of cationic polymers having a determined molecular weight range, the cationic polymers used in accordance with the present invention generally have a molecular weight ranging from 500 to 2,000,000, and preferably from 5,000 to 1,000,000.

These useful cationic polymers constitute a class of materials well known to the specialists in the field of cosmetology. Such cationic polymers are described principally in the following French patents and patent applications: 2.077.143, 1.492.597, 2.162.025, 2.280.361, 2.252.840, 2.368.508, 1.583.363, 2.080.759, 2.190.406, 2.320.330, 2.270.846, 2.316.271, 2.336.434, 2.189.434, 2.413.907, as well as in the following U.S. Pat. Nos.: 3,589,978; 4,031,307; 3,227,615; 2,961,347; 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945 and 4,027,020, incorporated herein by reference.

The cationic polymers employed in accordance with the present invention are principally polymers of the polyamine, polyaminoamide or quaternary polyammonium type (the amine or ammonia group being a part of the polymer chain or being linked to it) which provides, moreover, the characteristic of being incompatible with the gelifiable vehicles, in accordance with the definition of incompatibility which has been given above.

Representative polymers of this type, useful in the present invention, are principally:

1. copolymers of vinyl-pyrrolidone-acrylate or methacrylate or amino alcohol (quaternized or not), such as those sold under the name "Gafquat" by GAF, as for example, the "copolymer 845", "Gafquat 734 or 755" described principally in greater detail in French Pat. No. 2.077.143;

2. derivatives of cellulose ethers having quaternary ammonium groups such as those described in French Pat. No. 1.492.597 and principally the polymers sold under the name "JR" such as, "JR 125," "JR 400" and "JR 30M" and "LR", such as "LR 400" and "LR 30M" by Union Carbide, as well as cationic cellulose derivatives, such as "CELQUAT L.200" and "CELQUAT H 100" sold by National Starch;

3. cationic polysaccharides, described in U.S. Pat. Nos. 3,589,978 and 4,031,307 and in particular, "Jaguar C 13S" sold by Société Meyhall;

4. cationic polymers selected from the group consisting of (a) polymers containing units of the formula:

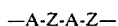

wherein

A represents a radical having two amine functions, preferably

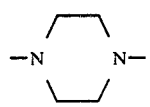

and

Z represents B or B';

B and B', each independently, represent a bivalent radical which is a straight or branched chain alkylene radical containing up to 7 consecutive carbon atoms in the principal chain, unsubstituted or substituted by hydroxyl groups and being able to have, moreover, oxygen, nitrogen or sulfur atoms, 1 to 3 aromatic rings and/or heterocycles; the oxygen, nitrogen and sulfur atoms being present in the form of an ether or thioether group, a sulfoxide, a sulfone, a sulfonium, an amine, an alkylamine, an alkenylamine, benzylamine, amine oxide, quaternary amine, amide, imide, alcohol, ester and/or urethane; the polymers and their process of preparation are described in French Pat. No. 2.162.025;

(b) polymers containing units of the formula:

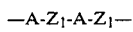

wherein

A represents a radical having two amine functions and, is preferably,

and $Z_1$ represents $B_1$ and $B'_1$, with $Z_1$ representing, at least once, the symbol $B'_1$;

$B_1$ represents a bivalent radical which is a straight chain or branched alkylene or hydroxyalkylene having up to 7 consecutive carbon atoms in the principal chain, $B'_1$ is a bivalent radical which is a straight chain or branched alkylene radical having up to 7 consecutive carbon atoms in the principal chain, unsubstituted or substituted by one or more hydroxy radicals and interrupted by one or more nitrogen atoms, the nitrogen atom being substituted by an alkyl chain having, optionally from 1 to 4 atoms and preferably 4 carbon atoms, interrupred optionally by an oxygen atom and having optionally one or more hydroxyl functions; these polymers and their process of preparation are described in French Pat. No. 2.280.361;

(c) quaternary ammonium salts and the oxidation products of the polymers of the above formulas indicated in (a) and (b);

5. crosslinked polyamino amides optionally alkylated selected from the group formed by at least one crosslinked polymer, obtained by crosslinking a polyaminopolyamide (A) prepared by the polycondensation of an acid compound with a polyamine, the acid compound being selected from:

(i) dicarboxylic organic acids, (ii) mono- and dicarboxylic aliphatic acids having an ethylenic double bond, (iii) esters of said acids, preferably esters of lower alkanols having 1 to 6 carbon atoms, and (iv) mixtures of the compounds defined in (i), (ii) and (iii).

The polyamine is selected from bis primary, mono- or di-secondary polyalkylene polyamines. 0 to 40 mole percent of this polyamine can be replaced by a bis-primary amine, preferably ethylene diamine or by a bis-secondary amine, preferably piperazine and 0 to 20 mole percent can be replaced by hexamethylenediamine. The crosslinking is carried out by means of a crosslinking agent (B) selected from the epihalohydrins, diepoxides, dianhydrides, unsaturated anhydrides and unsaturated bis derivatives. The crosslinking is characterized by the fact that it is effected by means of 0.025 to 0.35 mole of crosslinking agent per amine group of the polyamino-polyamide (A) and generally by means of 0.025 to about 0.2 mole and, in particular, by means of 0.025 to about 0.1 mole of crosslinking agent per amine group of the polyamino-polyamide (A). These polymers and their preparation are described in more detail in French Pat. No. 2.252.840.

Equally useful, on the one hand, are the polyamino-amides A and, on the other hand, the crosslinked polyamino-amides obtained by the crosslinking of a polyamino-amide (A, described above) by means of a crosslinking agent selected from the group consisting of:

(I) compounds selected from the group consisting of (1) bis halohydrins, (2) bis azetidinium, (b) bis haloacyl of diamines and (4) bis alkyl halides;

(II) oligomers obtained by the reaction of a compound (a) selected from the group consisting of (1) bis halohydrins, (2) bis azetidinium, (3) bis haloacyls of diamines, (4) bis alkyl halides, (5) epihalohydrin, (6) diepoxides, (7) bis unsaturated derivatives, with a compound (b) which is a bifunctional compound reactive vis-a-vis compound (a);

(III) the quaternization product of a compound selected from the group consisting of (a) the oligomers of (II) and having one or more tertiary amine groups, alkylated totally or partially with an alkylating agent (c) selected preferably from the group consisting of the chlorides, bromides, iodides, sulfates, mesylates and tosylates of methyl or ethyl, the chloride or bromide of benzyl, ethylene oxide, propylene oxide and glycidol, the crosslinking being carried out by means of 0.025 to 0.35 mole, in particular, by means of 0.025 or 0.2 mole and, more particularly, by means of 0.025 to 0.1 mole of crosslinking agent per amine group of the polyamino-amide.

These crosslinking agents and these polymers, as well as their method of preparation, are described in French Pat. No. 2.368.508;

6. the derivatives of polyamino-amides resulting from the condensation of polyalkylene polyamines with polycarboxylic acids followed by alkylation with a bifunctional agent such as adipic acid-dialkylaminohydroxyalkyl-dialkylene triamine copolymers in which the alkyl radical has 1-4 carbon atoms, described in French Pat. No. 1.583.363.

Representative derivatives include adipic acid-dimethylamino hydroxy-propyl-diethylenetriamine copolymers, sold under the tradename "Cartaretine F, F₄ or F₈" by Sandoz;

7. the polymers obtained by the reaction of a polyalkylene polyamine having two primary amine groups and at least one secondary amine group with a dicarboxylic acid selected from diglycolic acid and saturated aliphatic dicarboxylic acids having 3 to 8 carbon atoms. The molar ratio between the polyalkylene polyamine and the dicarboxylic acid is between 0.8:1 and 1.4:1. The resulting polyamide is reacted with epichlorohydrin in a malar ratio of epichlorohydrin relative to the secondary amine group of the polyamide between 0.5:1 and 1.8:1; mentioned in U.S. Pat. Nos. 3,227,615 and 2,961,347.

The polymers of this type are principally those sold under the tradename "Hercosett 57" by Hercules; or under the tradename "PD 170" or "Delsette 101" by Hercules in the case of the copolymer of adipic acid-/epoxypropyl diethylenetriamine;

8. cyclopolymers having a molecular weight of 20,000 to 3,000,000, such as homopolymers having as the principal constituent of the chain, units having formula (II) or (II'):

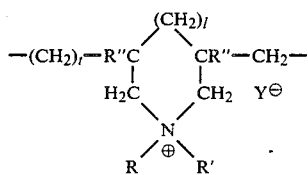

(II)

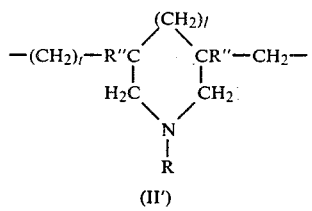

(II')

wherein l and t are equal to 0 or 1, l being equal to 0 if t=1, and l being equal to 1 if t=O, R" represents hydrogen or methyl, R and R' each indepedently representing alkyl having 1-22 carbon atoms, hydroxyalkyl wherein the alkyl groups has preferably 1-5 carbon atoms, a lower amidoalkyl group and where R and R' can represent together with the nitrogen atom to which they are attached heretocycle groups such as piperidinyl or morpholinyl, as well as copolymers having units of Formula II or II' and preferably units derived from acrylamide or diacetone acrylamide, $Y^{\ominus}$ is an anion, such as bromide, chloride, acetate, borate, citrate, tartrate, bisulfate, bisulfite, sulfate and phosphate.

Representative quaternary ammonium type polymers defined above, include the homopolymer of dimethyl diallyl ammonium chloride, sold under the tradename "Merquat 100", having a molecular weight lower than 100,000 and the copolymer of dimethyl diallyl ammonium chloride and acrylamide, having a molecular weight greater than 500,000 and sold under the tradename "Merquat 550" by Merck.

The polymers are described in French Pat. No. 2.080.759 and its certificate of addition No. 2.190.406.

9. quaternary polyammoniums containings units of formula

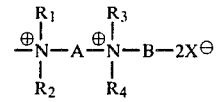

wherein $R_1$ and $R_2$, $R_3$ and $R_4$ equal or different, represent an aliphatic, alicyclic or arylaliphatic radical containing a maximum of 20 carbon atoms or a lower hydroxy aliphatic radical, or indeed the pairs $R_1$ and $R_2$, and $R_3$ and $R_4$ both or separately constitute with the nitrogen atoms to which they are attached, heterocycles containing optionally a second heteroatom other than nitrogen, or indeed $R_1$, $R_2$, $R_3$ and $R_4$ represent

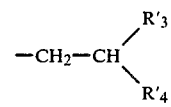

wherein $R'_3$ represents hydrogen or lower alkyl and $R'_4$ represents

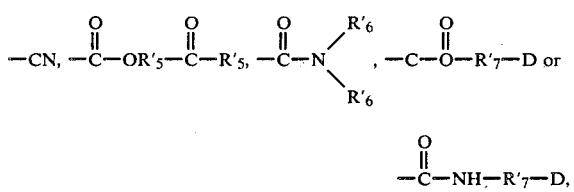

wherein $R'_5$ represents lower alkyl, $R'_6$ represents hydrogen or lower alkyl, $R'_7$ represents alkylene and D represents a quaternary ammonium group.

A and B can be any divalent group and can represent, principally, polymethylene groups containing 2 to 20 carbon atoms, linear or branched, saturated or unsaturated, and capable of containing, interposed in the principal chain, one or more aromatic rings such as —CH₂-C₆H₄-CH₂— or one or more groups of the formula —CH₂-Y-CH₂— wherein Y represents O, S, SO, SO₂,

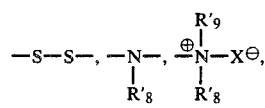

—CHOH—, —NH-CO-NH—, —CO-N(R'₈) or —CO-O— wherein $X^{\ominus}$ represents an anion derived from a mineral or organic acid, $R'_8$ represents hydrogen or lower alkyl, $R'_9$ represents lower alkyl or indeed A and $R_1$ and $R_3$ form with the two nitrogen atoms to which they are attached, a piperazine ring, or the pairs $R_1$, $R_3$ and/or $R_2$, $R_4$ form with A and with the two nitrogen atoms to which they are attached a cyclic or polycyclic group; moreover if A represents linear or branched alkylene or hydroxyalkylene, saturated or unsaturated, B can also represent a group of the formula —(CH₂)ₙ—CO-D-OC-(CH₂)ₙ— wherein D represents (a) a glycol residue of the formula —O-Z-O wherein Z represents a linear or branched hydrocarbon radical or a group selected from $$+CH_2-CH_2-O]_xCH_2-CH_2- \text{ or}$$

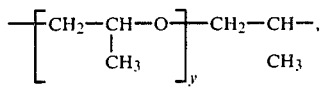

where x and y represent a whole number from 1 to 4, there representing a defined and unique degree of polymerization or any number from 1 to 4 representing an average degree of polymerization;

(b) a residue of a bis-secondary diamine such as one derived from piperazine having the formula

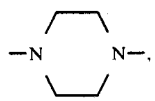

(c) a residue of a bis-primary diamine having the formula, —NH-Y-NH—, wherein Y represents a linear or branched hydrocarbon radical, or the bivalent radical, —CH$_2$-CH$_2$-S-S-CH$_2$-CH$_2$—, (d) a ureylene group of the formula —NH-CO-NH—; and X$^\ominus$ is an anion such as chloride or bromide.

These polymers have a molecular mass generally between 1,000 and 100,000.

Some polymers of type are described, in particular, in French Pat. Nos. 2.320.330, 2.270.846, French applications 76.20261 and 2.336.434 and U.S. Pat. Nos. 2,273,780; 2,375,853; 2,388,614; 2,454,547; 3,206,462; 2,261,002 and 2,271,378.

Other polymers of this type are described in the following U.S. Pat. Nos.: 3,874,870; 4,001,432; 3,929,990; 3,966,904; 4,005,193; 4,025,617; 4,025,627; 4,025,653; 4,026,945 and 4,027,020.

10. hompolymers or copolymers derived from acrylic or methacrylic acid and having as a unit:

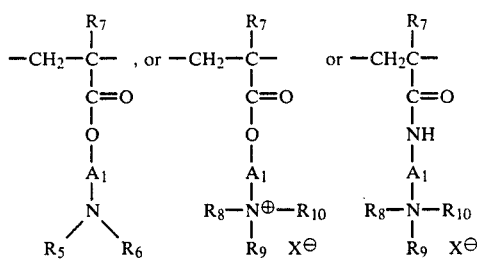

wherein

R$_7$ is H or CH$_3$,

A$_1$ is a linear or branched alkyl having 1-6 carbon atoms or hydroxyalkyl having 1-4 carbon atoms, R$_8$, R$_9$ and R$_{10}$, each independent, represent alkyl having 1-18 carbon atoms or benzyl, R$_5$ and R$_6$ represent hydroen or alkyl having 1-6 carbon atoms and X$_1$ represents halogen such as chloride or bromide, or a methosulfate.

Useful comonomers belong to the family of: acrylamide, methacrylamide, diacetone acrylamide, acrylamide and methacrylamide substituted on the nitrogen by lower alkyl, alkyl esters of acrylic and methacrylic acids, vinylpyrrolidone and vinyl esters.

As an example, there can be mentioned:
(1) the copolymer of acrylamide and beta methacryloyloxyethyl trimethylammonium methosulfate, sold under the tradenames "Reten 205, 210, 220 and 240" by Hercules,
(2) the copolymers of ethyl methacrylate, ollyl methacrylate and beatmethacryloyloxyethyldiethyl methylammonium methosulfate, referenced under the name "Quaternium 38" in the Cosmetic Ingredient Dictionary,
(3) the copolymer of ethyl methacrylate, abiethyl methacrylate and beta methacryloyloxyethyldiethyl methylammonium methosulfate, referenced under the name "Quaternium 37" in the Cosmetic Ingredient Dictionary,
(4) the polymer of beta methacryloyloxyethyl trimethylammonium bromide referenced under the name of "Quaternium 49" in the Cosmetic Ingredient Dictionary,
(5) the copolymer of beta methacryloyloxyethyl trimethylammonium methosulfate and beta methacryloyloxyethyl stearyldimethylammonium methosulfate referenced under the name of "Quaternium 42" in the Cosmetic Ingredient Dictionary,
(6) the copolymer of aminoethylacrylate phosphate/acrylate sold under the tradename "Catrex" by National Starch, and
(7) graft and crosslinked cationic copolymers having a molecular weight of 10,000 to 1,000,000 and preferably from 15,000 to 500,000, resulting from the copolymerization of:
(a) at least one cosmetic monomer,
(b) dimethylaminoethyl methacrylate,
(c) polyethylene glycol and
(d) a polyunsaturated crosslinking agent, described in French patent 2.189.434

The cosmetic monomer can be of a very diverse type, for example, a vinyl, allylic or methallylic ester, an acrylate or methacrylate of a saturated alcohol having 1-8 carbon atoms, an alkyl vinyl ether, an olefin, a vinyl heterocyclic derivative, a dialkyl maleate or N,N-dialkyl-aminoalkyl maleate or an anhydride or an unsaturated acid.

Other useful cationic polymers are, for example, polyalkylene imines and, in particular, polyethyleneimines, polymers containing in the chain vinylpyridine or vinylpyridinium units, condensates of polyamines and epichlorohydrin, quaternary polyureylenes and chitin derivatives.

In the process of the present invention, the cationic polymer can be added to the oxidizing solution at the moment of use, or indeed the mixtures can be prepared in advance. In any case, it is this mixture which is added to the hair dye or hair bleach vehicle or support.

The invention also relates to a composition to be used in the process such as defined above, said composition comprising, in an appropriate container, the said gelifiable liquid vehicle and the said oxidizing solution, combined in a package permitting their method of use.

The cationic polymer can be dissolved in the oxidizing solution. It can also be provided separately, the cationic polymer being placed in a third container, either alone, or in solution in a solvent. Before implementing the process of the invention, the cationic polymer is admixed with the oxidizing solution.

The invention also relates, in particular, to a composiiton such as defined above, and principally a composition containing the cationic polymer dissolved in the oxidizing solution, wherein the cationic polymer is selected from the group consisting of homopolymers of dimethyl diallyammonium chloride and polymers having units of the formula:

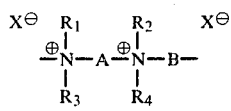 (I)

wherein $R_1$ and $R_2$ represent alkyl having 1-3 carbon atoms, $R_3$ and $R_4$ represent alkyl or hydroxyalkyl, having 1-3 carbon atoms, $R_2$ and $R_4$ can also represent alkyl having 4-8 carbon atoms when $R_1=R_3=CH_3$, and in this case $R_2$ is equal to $R_4$, and $R_4$ can also represent benzyl, cyclohexyl or alkyl having 4-12 carbon atoms when $R_1=R_2=R_3=CH_3$, A and B, each independently, represent linear or branched alkylene or alkenylene having 2 to 20 carbon atoms in the chain, $-(CH_2)_n-O-(CH_2)_n-$, $-(CH_2)_m-NH-CO-NH-(CH_2)_m-$, $-CH_2-CH(OH)-CH_2-$ or $-CH_2-C_6H_4-CH_2-$, n and m being whole numbers equal to 2 or 3, and X represents an anion.

The invention also relates to a process of preparing a hair dye or hair bleach composition.

The invention further relates to a process for dyeing or bleaching hair comprising applying to the hair, in an amount effective to produce the desired result and in accordance with known techniques for applying such compositions, the composition resulting from the process of the present invention.

The composition is permitted to remain in contact with the hair for a period of time ranging between about 5 to 45 minutes, preferably between 15 and 30 minutes. Thereafter the hair is rinsed.

The following non-limiting examples illustrate the invention.

In these examples:

(a) cationic polymer 1 is constituted by units of the formula:

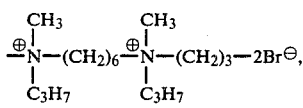

(b) cationic polymer 2 is constituted by units of the formula:

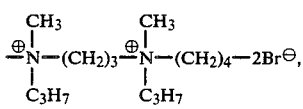

(c) cationic polymer 3 is constituted by units of the formula:

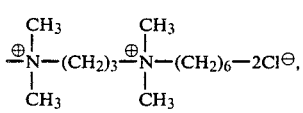

(d) cationic polymer 4 is constituted by units of the formula:

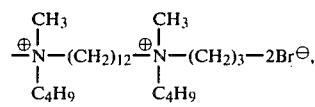

(e) cationic polymer 5 is constituted by units of the formula:

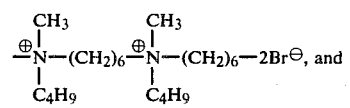

(f) "Mirapol A15" is constituted by units of the formula:

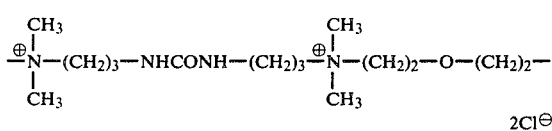

EXAMPLE 1

Preparation of a hair bleach composition

Initially there is prepared:

(a) a gelifiable vehicle having the following composition:

oleyl alcohol glycerolated with 2 moles of glycerol: 20 g oleyl alcohol glycerolated with 4 moles of glycerol: 15 g propylene glycol: 5 g monobutyl ether of ethylene glycol: 11 g Masquol DTPA (pentasodium salt of diethylene triamino pentacetic acid) aqueous solution containing 40% active material: 2.5 g Ammonia, 22° Be': 10 g Water, sufficient amount for: 100 g and (e) an oxidizing solution having the following composition:

cetyl alcohol: 1.5 g cetyl stearyl alcohol oxyethylenated with 15 moles of ethylene oxide: 2.5 g ortho-oxyquinolein sulfate: 0.05 g cationic polymer 1: 2 g $H_2O_2$ (200 vol) sufficient amount for: 20 vol.

HCl, sufficient amount for pH=3

Water, sufficient amount for: 100 g

There are mixed in a bowl, before use, 40 g of the gelifiable vehicle with 40 g of the oxidizing solution.

There results a gel which adheres quite well to the hair during application with the aid of a brush. The gel is permitted to remain in contact with the hair for 30 to 45 minutes after which the hair is rinsed.

The wet har combs easily and has a silky touch. After drying, the hair is shiny and lively; it has body, and a silky feel; and is easy to comb.

The hair is, in a general manner, in a much better condition than after bleaching with the same composition without the cationic polymer.

On deep chestnut colored hair, after bleaching, a deep blond coloration is obtained.

EXAMPLE 2

Preparation of a hair bleach composition (a) gelifiable vehicle having the following composition:

Synthetic primary alcohol having 13-15 carbon atoms, oxyethylenated with 2.8 moles of ethylene oxide and sold under the tradename "UKANIL 25" by P.C.U.K.: 30 g Synthetic primary alcohol having 9-11 carbon atoms, oxyethylenated with 6 moles of ethylene oxide, sold under the name "UKANIL 50" by P.C.U.K.: 25 g Ethyl alcohol, 96°: 11 g Masquol DPTA (aqueous solution containing 40% active material): 2 g Ammonia, 22° Be': 12 g Water, sufficient amount for: 100 g (b) oxidizing solution having the following composition:

oxyethylenated cetylstearyl alcohol sold under the tradename "SINNOWAX AO" by Henkel: 4 g ortho oxyquinolein sulfate: 0.05 g cationic polymer 2: 3 g $H_2O_2$-200 vol. sufficient for: 20 vol.

HCl, sufficient for pH=3 water, sufficient amount for: 100 g

There are mixed in a bowl, before use, 40 g of the gelifiable vehicle with 40 g of the oxidizing solution.

There results a gel which adheres well to hair during application using a brush. The gel is permitted to remain in contact with the hair for 30-45 minutes. Thereafter the hair is rinsed.

The wet hair combs easily and has a silky touch. After drying, the hair is shiny, lively, has body, its touch is silky and it combs easily.

The hair is, in a general fashion, in a much better condition than after bleaching with the same composition without the cationic polymer.

On deep chestnut colored hair, after bleaching, a deep blond coloration is obtained.

EXAMPLE 3

Preparation of a hair bleach composition (a) gelifiable vehicle having the following composition:

Nonyl phenol oxyethylenated with 4 moles of ethylene oxide: 25 g nonyl phenol oxyethylenated with 9 moles of ethylene oxide: 20 g Masquol DTPA (aqueous solution containing 40% active material): 2.6 g monobutyl ether of ethylene glycol: 7 g propylene glycol: 10 g ammonia, 22°Be' 10 g Water, sufficient amount for: 100 g (b) oxidizing solution having the following composition:

oxyethylenated cetylstearyl alcohol, sold under the tradename "Sinnowax AO" by Henkel: 4 g ortho oxyquinolein suflate: 0.07 g cationic polymer 3: 1.5 g $H_2O_2$-200 vol., sufficient for 20 vol.

HCl, sufficient for pH=3:

Water, sufficient amount for: 100 g

There are placed in a package having seveal compartments and fitted with a means for use, a flask containing 40 g of the gelifiable vehicle and a flask containing 40 g of the oxidizing solution.

There are mixed in a bowl, before use, 40 g of the gelifiable vehicle with 40 g of the oxidizing solution.

There results a gel which adheres well to hair during application using a brush. The gel is permitted to remain in contact with the hair for 30 to 45 minutes. Thereafter, the hair is rinsed.

The wet hair combs easily and has a silky touch. After drying, the hair is shiny and lively; has body (volume) and a silky touch; and combs easily.

The hair is, in a general manner, in a much better condition than after bleaching with the same composition, without the cationic polymer.

On deep chestnut colored hair, after bleaching, a deep blond coloration is obtained.

EXAMPLE 4

Preparation of a hair bleach composition (a) gelifiable vehicle having the following composition:

nonyl phenol oxyethylenated with 4 moles of ethylene oxide: 25 g nonyl phenol oxyethylenated with 9 moles of ethylene oxide: 20 g Masquol DTPA (aqueous solution containing 40% active material): 2.6 g monobutyl ether of ethylene glycol: 7 g propylene glycol: 10 g ammonia, 22°Be': 10 g Water, sufficient amount for: 100 g (b) oxidizing solution having the following composition:

oxyethylenated cetylstearyl alcohol, sold under the tradenamen "Sinnowax AO" by Henkel: 4 g ortho oxyquinolein sulfate: 0.06 g cationic polymer 4: 2 g $H_2O_2$-200 vol., sufficient for 20 vol.

HCl, sufficient for pH=3

Water, sufficient amount for 100 g

There are mixed in a bowl, before use, 40 g of the gelifiable vehicle with 40 g of the oxidizing solution.

There results a gel which adheres well to the hair during application using a brush. The gel is permitted to remain in contact with the hair for 30 to 45 minutes. Thereafter the hair is rinsed.

The wet hair combs easily and its touch is silky. After drying, the hair is shiny, lively and has body (volume); its touch is silky and it combs easily.

The hair is, in a general fashion, in a much better condition than after bleaching with the same composition without the cationic polymer.

On deep chestnut colored hair, after bleaching, a deep blond coloration is obtained.

EXAMPLE 5

Preparation of an oxidation dye composition for the hair (a) gelifiable vehicle having the following composition:

synthetic primary alcohol having 13-15 carbon atoms, oxyethylenated with 2.8 moles of ethylene oxide, sold under the tradename "UKANIL 25" by P.C.U.K.: 15 g synthetic primary alcohol having 9-11 carbon atoms, oxyethylenated with 6 moles of ethylene oxide, sold under the tradename "UKANIL 50" by P.C.U.K.: 10 g
oleic diethanolamide: 10 g
ethylenediamine tetracetic acid: 1 g
ethyl alcohol—96°: 13.5 g
propylene glycol: 2 g
ammonia—22°Be': 10 g
sodium bisulfite (d=1.32): 1 ml
4-N, (β-methoxyethyl)amino aniline dihydrochloride: 1.6 g
p-aminophenol: 0.3 g
resorcinol: 0.2 g
m-aminophenol: 0.25 g
5,N-(β-hydroxyethyl)amino2-methylphenol: 0.02 g
2,4-diamino phenoxy ethanol dihydrochloride: 0.02 g
water, sufficient amount for: 100 g
(b) oxidizing solution having the following composition:
$H_2O_2$-200 vol., sufficient for: 20 vol.
ortho oxyquinolein sulfate: 0.05 g
cationic polymer 2: 3 g
HCl, sufficient for pH=2:
Water, sufficient amount for: 100 g There are mixed in an applicator 30 g the gelifiable vehicle with 30 g of the oxidizing solution containing the cationic polymer.

The resulting gel is applied to the hair and is permitted to remain in contact therewith for 30 minutes. Thereafter the hair is rinsed. The thus treated hair combs easily and its touch is silky. The hair is then set and dried. The hair is shiny and lively; it has body (volume); its touch is silky and it combs easily.

There is obtained an ashen light chestnut coloration.

EXAMPLE 6

Preparation of an oxidation dye compositon for the hair (a) gelifiable vehicle having the following composition:
oleyl alcohol glycerolated with 2 moles of glycerol: 20 g
oleyl alcohol glycerolated with 4 moles of glycerol: 20 g
oleic diethanolamide: 12 g
ethyl alcohol—96°: 12 g
monobutyl ether of ethylene glycol: 1 g
propylene glycol: 2 g
ethylene diamine tetracetic acid: 1 g
ammonia-22°Be': 10 g
sodium bisulfite (d=1.32): 1 ml
4,N-(β-methoxyethyl)amino aniline dihydrochloride: 1.6 g
p-aminophenol: 0.3 g
resorcinol: 0.2 g
m-aminophenol: 0.25 g
5,N-(β-hydroxyethyl)amino-2-methylphenol: 0.02 g
2,4-diaminophenoxyethanol dihydrochloride: 0.02 g
water, sufficient amount for: 100 g
(b) oxidizing solution having the following composition:
$H_2O_2$-200 vol., sufficient for 20 vol.
ortho oxyquinolein sulfate: 0.07 g
cationic polymer-"Mirapol A15", sold by Miranol 1.5 g
HCl, sufficient for pH=3
Water, sufficient amount for 100 g There are mixed in an applicator 30 g of the gelifiable vehicle with 30 g of the oxidizing solution containing the cationic polymer.

The resulting gel is applied to the hair and permitted to remain in contact therewith for 30 minutes. Thereafter the hair is rinsed. The thus treated hair combs easily and is silky to the touch. The hair is set and then dried. The hair is shiny, lively and has body (volume); its touch is silky and it combs easily.

There is obtained as ashen light chestnut coloration.

EXAMPLE 7

Preparation of a hair dye composition (a) gelifiable support having the following composition:
nonyl phenol oxyethylenated with 4 moles of ethylene oxide: 18 g
nonyl phenol oxyethylenated with 9 moles of ethylene oxide: 13 g
oleic diethanolamide: 9.5 g
ethylene diamine tetracetic acid: 0.8 g
ethyl alcohol-96°: 12 g
propylene glycol: 5 g
ammonia—22°Be': 12 g
sodium bisulfite (d=1.32): 1 ml
4,N-(β-methoxyethyl)amino aniline dihydrochloride: 1.6 g
p-aminophenol: 0.3 g
resorcinol: 0.2 g
m-aminophenol: 0.25 g
5,N-(β-hydroxyethyl)-amino-2-methyl phenol: 0.02 g
2,4-diamino phenoxy ethanol dihydrochloride: 0.02 g
water, sufficient amount for: 100 g
(b) oxidizing solution having the following composition:
$H_2O_2$-200 vol., sufficient for 20 vol.
ortho oxyquinolein sulfate: 0.05 g
cationic polymer 5: 2 g
HCl, sufficient for pH=3
Water, sufficient amount for: 100 g There are mixed in an applicator 30 g of the gelifiable vehicle with 30 g of the oxidizing solution containing the cationic polymer.

The resulting gel is applied to the hair and permitted to remain in contact therewith for 30 minutes. Thereafter the hair is rinsed. The hair thus treated is easy to comb and it is silky to the touch. The hair is then set and dried. The hair is shiny, lively and has body; its touch is silky and it is easy to comb.

There is obtained an ashen light chestnut coloration.

EXAMPLE 8

Preparation of a hair dye composition (a) gelifiable vehicle having the following composition:
oleyl alcohol glycerolated with 2 moles of glycerol: 20 g
oleyl alcohol glycerolated with 4 moles of glycerol: 15 g
oleic diethanolamide: 8 g
Masquol DTPA (aqueous solution containing 40% active material): 2.5 g
monobutylether of ethylene glycol: 12 g
propylene glycol: 7 g
ammonia-22°Be': 11 g
sodium bisulfate (d=1.32): 1 ml 4,N-(β-methoxyethyl)amino aniline dihydrochloride: 1.6 g
p-aminophenol: 0.3 g
resorcinol: 0.2 g
m-aminophenol: 0.3 g
5,N-(β-hydroxyethyl)amino 2-methyl phenol: 0.02 g
2,4-diaminophenoxy ethanol dihydrochloride: 0.02 g
water, sufficient amount for: 100 g
(b) oxidizing solution having the following composition:
$H_2O_2$-200 vol., sufficient for 20 vol.
ortho oxyquinolein sulfate: 0.05 g
cationic polymer 3: 2 g
HCl, sufficient for pH=3
water, sufficient amount for: 100 g There are mixed in an applicator 30 g of the gelifiable vehicle with 30 g of the oxidizing solution containing the cationic polymer.

The resulting gel is applied to the hair and permitted to remain in contact therewith for 30 minutes. Thereafter the hair is rinsed. The thus treated hair combs easily and has a silky touch. The hair is then set and dried. The hair is shiny, lively and has body (volume). Its touch is silky and it combs easily.

There is obtained as ashen light chestnut coloration.

EXAMPLE 9

Preparation of a hair bleach composition (a) gelifiable vehicle having the following composition:
nonyl phenol oxyethylenated with 4 moles of ethylene oxide: 30 g
nonyl phenol oxyethylenated with 9 moles of the ethylene oxide: 25 g
monobutyl ether of ethylene glycol: 10 g
Masquol DTPA (aqueous solution containing 40% active material): 2.4 g
ammonia-22°Be': 11 g
water, sufficient amount for 100 g
(b) oxidizing solution having the following composition:
$H_2O_2$-200 vol., sufficient for: 22 vol.
ortho oxyquinolein sulfate: 0.065 g
HCl, sufficient for pH=3:
water, sufficient amount for: 100 g
(c) polymer solution. An aqueous solution containing 60% of cationic polymer 3.

There are placed in a package having several compartments fitted with a means for use, a flask containing 40 g of the gelifiable vehicle defined in (a) above, a flask containing 36 g of the oxidizing solution defined in (b) above, and a flask containing 4 g of the solution defined in (c) above.

To use this composition, there are mixed, just before use, 4 g of solution (c) in 36 g of solution (b). There are then introduced 40 g of solution (b).

The resulting gel, which adheres well to the hair during application using a brush, is permitted to remain in contact with the hair for 30 to 45 minutes. Thereafter the hair is rinsed.

The wet hair combs easily and is silky to the touch. After drying, the hair is shiny, lively and has body; its touch is silky and it combs easily.

The hair is, in a general fashion, in much better condition than after bleaching with the same composition without the cationic polymer.

On deep chestnut colored hair, after bleaching, a deep blond coloration is obtained.

What is claimed is:

1. A process for preparing a clear gel for bleaching the hair comprising
   (a) admixing a gelifiable liquid consisting essentially of a mixture of
   (1) a non-ionic compound selected from the group consisting of
   (i) polyoxyethylenated fatty alcohol having 8-18 carbon atoms and oxyethylenated with 2-30 moles of ethylene oxide,
   (ii) polyglycerolated fatty alcohol having 8—18 carbon atoms and glycerolated with 1-6 moles of glycerol,
   (iii) polyoxyethylenated alkyphenol wherein the alkyl moiety has 8-9 carbon atoms and oxyethylenated with 2-30 moles of ethylene oxide, and
   (iv) polyglycerolated alkyphenol wherein the alkyl moiety has 8-9 carbon atoms and glycerolated with 4-6 moles of glycerol and
   (2) a solvent selected from the group consisting of a lower aliphatic alcohol, a glycol and a glycol ether, with
   (b) an oxidizing solution comprisng a solution of $H_2O_2$ and an incompatible cationic polymer dissolved therein, said incompatible cationic polymer being one which when mixed with an incompatible polymer test support in an amount from 0.5 to 5 weight percent of said test support results in the formation of a cloud or precipitate, or a separation of said test support into two phases, said test support consisting essentially of 20 g of a nonyl phenol oxyethylenated with 9 moles of ethylene oxide, 24 g of nonyl phenol oxyethylenated with 4 moles of ethylene oxide, 9 g of monobutylether of ethylene glycol, 10 g of propylene glycol, 2.4 g of 40 weight percent aqueous solution of the pentasodium salt of diethylene triamine pentacetic acid, 10 g of ammonia 22° Be' and water is an amount sufficient for 100 g,
   the resulting admixture containing 5 to 60 weight percent of said nonionic compound and 2 to 20 weight percent of said solvent and wherein said compatible cationic polymer is present in said oxidizing solution in an amount sufficient so that the concentration of said incompatible polymer is between 0.01 and 10 weight percent based on the total weight of the admixture resulting from admixing said gelifiable liquid and said oxidizing solution.

2. The process of claim 1 wherein the resulting admixture has a pH of about 8 to 11.

3. The process of claim 2 wherein said pH is obtained by the addition of, as an alkalizing agent, soda, potash, ammonia, monoethanolamine, diethanolamine triethanolamine, mono-isopropanolamine, diisopropanolamine, 2-amino-methyl-1,3-propanediol, 2-amino-2methyl-1-propanol or a mixture thereof.

4. The process of claim 1 wherein the concentration of $H_2O_2$ in said oxidizing solution is from 20 to 60 volumes.

5. The process of claim 1 wherein said oxidizing solution is added to the resulting admixture of said gelifiable liquid and solvent in a ratio of 0.5-5 to 1, by volume.

6. The process of claim 1 wherein said incompatible cationic polymer is added to said oxidizing solution at the time of use and the resulting mixture is added to said gelifiable liquid and said solvent.

7. A two part hair bleaching compositon consisting of as a first part, a gelifiable liquid consisting essentially of a mixture of (1) a non-ionic compound selected from the group consisting of
   (i) polyoxyethylenated fatty alcohol having 8–18 carbon atoms and oxyethylenated with 2–30 moles of ethylene oxide,
   (ii) polyglycerolated fatty alcohol having 8–18 carbon atoms and glycerolated with 1–6 moles of glycerol,
   (iii) polyoxyethylenated alkylphenol wherein the alkyl moiety has 8–9 carbon atoms and oxyethylenated with 2–30 moles of ethylene oxide, and
   (iv) polyglycerolated alkylphenol wherein the alkyl moiety has 8–9 carbon atoms and glycerolated with 4–6 moles of glycerol and
   (2) a solvent selected from the group consisting of a lower aliphatic alcohol, a glycol and a glycol ether, and
as a second part, an oxidizing solution comprising a solution of $H_2O_2$ and an incompatible cationic polymer dissolved therein, said incompatible cationic polymer being one which when mixed with an incompatible polymer test support in an amount from 0.5 to 5 weight percent of said test support results in the formation of a cloud or precipitate, or a separation of said test support into two phases, said test support consisting essentially of 20 g of nonyl phenol oxyethylenated with 9 moles of ethylene oxide, 24 g of nonlyl phenol oxyethylenated with 4 moles of ethylene oxide, 9 g of monobutylether of ethylene glycol, 10 g of propylene glycol, 2.4 g of 40 weight percent aqueous solution of the pentasodium salt of diethylene triamine pentacetic acid, 10 g of ammonia 22° Be' and water in an amount sufficient for 100 g, said two parts being packaged in one package and whereby on admixture of said first part to said second part, the resulting admixture contains 5 to 60 weight percent of said nonionic compound, 2 to 20 weight percent of said solvent and 0.01 to 10 weight percent of said incompatible cationic polymer.

* * * * *